United States Patent
Kluge

(10) Patent No.: US 8,518,071 B2
(45) Date of Patent: Aug. 27, 2013

(54) DRIVING DEVICE FOR A DEVICE FOR THE LOCAL PUNCTURING OF A SKIN AND A METHOD FOR OPERATING THE DRIVING DEVICE

(75) Inventor: Jörn Kluge, Teltow (DE)

(73) Assignee: MT DERM GmbH, Berlin (DE)

( * ) Notice: Subject to any disclaimer, the term of this patent is extended or adjusted under 35 U.S.C. 154(b) by 2176 days.

(21) Appl. No.: 11/484,858

(22) Filed: Jul. 12, 2006

(65) Prior Publication Data

US 2007/0083223 A1    Apr. 12, 2007

(30) Foreign Application Priority Data

Jul. 12, 2005   (EP) .................................... 05015074

(51) Int. Cl.
    *A61B 17/34*    (2006.01)
(52) U.S. Cl.
    USPC ........................................................ 606/185
(58) Field of Classification Search
    USPC ................... 606/169, 184, 185, 186; 604/22;
    81/9.22; 30/362
    See application file for complete search history.

(56) References Cited

U.S. PATENT DOCUMENTS

| | | | |
|---|---|---|---|
| 4,671,277 A | 6/1987 | Beuchat | |
| 4,782,725 A | 11/1988 | Spaulding | |
| 5,054,339 A | 10/1991 | Yacowitz | |
| 5,471,102 A | 11/1995 | Becker et al. | |
| 5,976,167 A | 11/1999 | Lee | |
| 6,345,553 B1 | 2/2002 | Adler et al. | |
| 2005/0277973 A1* | 12/2005 | Huang et al. | 606/185 |

* cited by examiner

*Primary Examiner* — Thomas McEvoy
(74) *Attorney, Agent, or Firm* — Smith Patent Office

(57) ABSTRACT

The invention concerns a driving device for a device for the local puncturing of a skin, particularly for the application of permanent make-up or a tattoo, as well as a method for operating the driving device. The driving device comprises a drive mechanism for producing a repetitive thrust movement at a frequency, which is usable for the retraction/extension of a puncturing mechanism, a detection apparatus with which a parameter is detectable, which indicates a resistance force acting against the repetitive thrust movement, a setting apparatus with which, for the case that a changed resistance force is detected with the detection apparatus, can be pre-set by a user into an operating mode of increased frequency in which the frequency is increased after detection of the changed resistance force, or an operating mode of reduced frequency in which the frequency is reduced after detection of the changed resistance force, and a control apparatus coupled to the detection apparatus and the setting apparatus, the control apparatus automatically causes the frequency change of the increased frequency mode and the reduced frequency mode.

7 Claims, 1 Drawing Sheet

Figure 1:
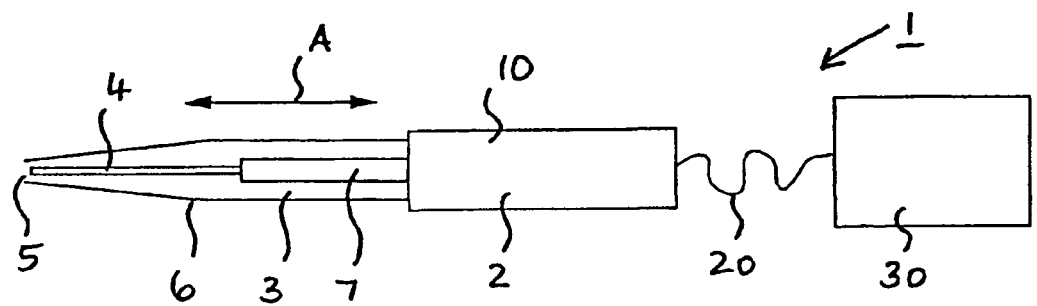

DRIVING DEVICE FOR A DEVICE FOR THE LOCAL PUNCTURING OF A SKIN AND A METHOD FOR OPERATING THE DRIVING DEVICE

BACKGROUND OF THE INVENTION

The invention refers to a driving device for a device for the local puncturing of a skin, particularly for the application of permanent make-up or a tattoo, and a method for operating the driving device.

Devices for the local puncturing of a skin are used, for example, for applying permanent make-up or a tattoo on human or animal skin and normally comprise a driving device with drive means for producing a repetitive thrust movement that is used in a module, coupled to the drive means, for the retraction and extension of puncturing means in order to puncture the skin, onto which the permanent make-up or the tattoo is to be applied. The puncturing means are normally a needle or a needle system that comprises several needles. After puncturing the skin, a coloring material routed along the puncturing means to the puncturing location can penetrate the skin surface. Such devices are described, for example, in the document U.S. Pat. No. 6,345,553.

When puncturing the skin to be treated, the thrust movement of the needle/of the needle system is confronted with a resistance force by the skin constituents. This resistance force depends on the individual characteristics of the skin in the surface area to be punctured. With known devices for applying permanent make-up or a tattoo, and with the help of a selection switch, a pre-specified repetition or repeating frequency of the repetitive/repeating thrust movement and subsequently the frequency of the skin puncturing per time unit can be stipulated, which is maintained at a constant level independent of the resistance force acting against the repetitive thrust movement. This is performed by re-regulation of the current/voltage values applied to the drive means for the purpose of maintaining a constant repetition frequency, even if there is a change in the resistance force resulting from changed skin characteristics. If such a constant maintenance of the repetition frequency is not envisaged, a drop of the repetition frequency can occur as a result of the increased resistance.

A skin area where an increased resistance force acts against the puncturing is described as a "harder skin". During the transition into such a skin area, a non-uniform color deposition for the permanent make-up or for the tattoo can occur.

In the document U.S. Pat. No. 5,976,167, a needle device for the treatment of chronic muscle pains is described. The needle device comprises a needle for the intra-muscular stimulation as well as a thrust tool for accommodating the needle. With the help of a motor, the needle is put into a repetitive thrust movement by means of the thrust tool.

The subject-matter of the document U.S. Pat. No. 5,054,339 is the supply of tattooing color material from a vessel to a tattooing needle. The supply velocity of the color material to the needle is controlled by a pump.

The documents U.S. Pat. No. 4,782,725 and U.S. Pat. No. 4,671,277 each describe a tattooing device where the velocity and/or the repetition frequency of the thrust movement of the tattooing needle is controlled. The control is performed manually.

Finally, with one tattooing device described in the document U.S. Pat. No. 5,471,102, the repetition frequency is stipulated on the basis of switching parameters of a circuit arrangement controlling the needle movement.

SUMMARY OF THE INVENTION

It is the task of the invention to state and present a driving device for a device for the local puncturing of a skin, particularly for the application of permanent make-up or a tattoo and a method for the operation of the driving device, which allow an individual adaptation to the different and, depending on the circumstances, repeatedly changing application conditions and/or the desired results during the process for the local puncturing of the skin.

This task is solved according to the invention by means of a driving device according to the driving device for the local puncturing of a skin, particularly for the application of permanent make-up or a tattoo, with a drive means for producing a repetitive thrust movement which is usable for the retraction/extension of puncturing means, comprising, a detection apparatus with which a parameter is detectable that indicates a resistance force acting against the repetitive thrust movement; a setting apparatus with which, for the case that a changed resistance force is detected with the detection apparatus, by a user for the drive means, an operating mode change into an operating mode of increased repeating frequency in which the repeating frequency of the repetitive thrust movement compared with the repeating frequency is increased before the detection of the changed resistance force, or an operating mode change into an operating mode of reduced repeating frequency can be pre-set in which the repeating frequency of the repetitive thrust movement compared with the repeating frequency is decreased before detection of the change resistance force; and a control apparatus coupled to the detection apparatus and the setting apparatus, with which the operating mode change into the operating mode of increased repeating frequency or into the operating mode of reduced repeating frequency is controlled corresponding to a pre-setting of the setting apparatus.

The detection apparatus is configured in order to detect a power input of the drive means. The detection apparatus is also configured in order to detect a power input of the drive means. In the present invention, the drive means can comprise a brush motor, and the detection apparatus can be configured to detect a commutation frequency of the brush motor.

The drive means are configured to maintain the repeating frequency at an essentially constant level and this can be changed depending on conditions in the different operating modes.

The control apparatus can be configured to control, during the operation mode change, the increased/reduced repeating frequency in the operating mode of increased repeating frequency/reduced repeating frequency depending on at least one measuring value for the detected parameter.

Also, the control apparatus is configured to change the operating mode into the one of the preset operating modes, set by the setting apparatus, if and when the detected parameter indicates an increase in the resistance force.

The objects of the invention are also solved by a method for the operation of a driving device for a device for the local puncturing of a skin, particularly for the application of permanent make-up or a tattoo, where the driving device has drive means for producing a repetitive thrust movement that is usable for the retraction/extension of puncturing means, and where the method comprises the following steps, detection of a parameter with a detection apparatus, which indicates a resistance force acting against the repetitive thrust movement; and control of an operating mode change with the help of a control apparatus coupled to the detection apparatus and the drive means into an operating mode of increased repeating frequency or an operating mode of reduced repeating frequency in accordance with a pre-setting of a setting apparatus; where the setting apparatus for the case that a changed resistance force is detected with the detection apparatus, is pre-set by a user so that the operating mode change is selectively stipulated in the operating mode of increased repeating frequency, in which the repeating frequency of the repetitive thrust movement is increased compared with the repeating frequency before detection of the changed resistance force, or in the operating mode of reduced repeating frequency in which the repeating frequency of the repetitive thrust movement is reduced compared with the repeating frequency before the detection of the change resistance force.

The repeating frequency, before detection of the changed resistance force, is essentially kept at a constant level when set in the increased frequency mode and in the reduced frequency mode.

The control apparatus during operation mode change, is changed depending on at least one measured value for the detected parameter.

In one embodiment, the control apparatus changes the operation mode into the operation mode which is pre-set using the setting apparatus, if and when the detected parameter is indicated, such as from an increase in the resistance force.

The control apparatus also can send an acknowledgement to the user before the operation mode change. The control apparatus can also receive an acknowledgement from the user before the operation mode is changed.

The present invention also is related to a device for the local puncturing of a skin with a drive means for producing a repetitive thrust movement which is for the retraction/extension of a puncturing means, wherein the device comprises a detection apparatus detecting a parameter indicative of a resistance force acting against the puncturing means; a setting apparatus for setting different operation modes that are operable when said detection apparatus measures a change in the resistive force, the different operation modes including 1) an increased frequency mode where a frequency of the device is increased when said detection apparatus measures an increased resistive force, and 2) a reduced frequency mode were a frequency of the device is reduced when said detection apparatus measures an increased resistive force; and a control apparatus coupled to the detection apparatus and the setting apparatus, said control apparatus controls the operating mode change into the increased frequency mode or into the reduced frequency mode corresponding to a pre-set condition of the setting apparatus.

The present invention also is related to a device for the local puncturing of a skin with a drive means for producing a repetitive thrust movement which is for the retraction/extension of a puncturing means, wherein the device comprises a detection apparatus detecting a parameter indicative of a resistance force acting against the puncturing means; a setting apparatus for setting different operation modes that are operable when said detection apparatus measures a change in the resistive force, the different operation modes including 1) an increased frequency mode where a frequency of the device is increased when said detection apparatus measures a decreased resistive force, and 2) a reduced frequency mode were a frequency of the device is reduced when said detection apparatus measures a decreased resistive force; and a control apparatus coupled to the detection apparatus and the setting apparatus, said control apparatus controls the operating mode change into the increased frequency mode or into the reduced frequency mode corresponding to a pre-set condition of the setting apparatus. The control functions based on measuring an increased resistive force and a decreased resistive force can also be combined to include multiple operation modes in one control apparatus.

According to one aspect of the invention, a driving device is created for a device for the local puncturing of a skin, particularly for the application of permanent make-up or a tattoo with drive means for producing a repetitive movement which is usable for the extension and retraction of puncturing means, where the driving device has the following features: a detection apparatus with which a parameter is detectable that indicates a resistance force acting against the repetitive thrust movement; a setting apparatus with which, for the case that a changed resistance force is detected with the detection apparatus, can be pre-set by a user for the drive means, an operating mode change into an operating mode of increased repeating frequency in which the repeating frequency of the repetitive thrust movement compared with the repeating frequency is increased before the detection of the changed resistance force, or an operating mode change into an operating mode of. reduced repeating frequency in which the repeating frequency of the repetitive thrust movement compared with the repeating frequency is decreased before detection of the change resistance force; and a control apparatus, coupled to the detection apparatus and the setting apparatus, with which the operating mode change into the operating mode of increased repeating frequency or into the operating mode of decreased repeating frequency is controlled corresponding to pre-setting of the setting apparatus.

According to a further aspect of the invention, a method is created for the operation of a driving device for a device for the local puncturing of a skin, particularly for the application of permanent make-up or a tattoo where the driving device comprises drive means for producing a repetitive thrust movement for the extension and retraction of puncturing means and where the method has the following steps: detection of a parameter with a detection apparatus, which indicates a resistance force acting against the repetitive thrust movement during extension; and control of an operating mode change with the help of a control apparatus, coupled to the detection apparatus and the drive means, into an operating mode of increased repeating frequency or an operating mode of decreased repeating frequency corresponding to the pre-setting of a setting apparatus; where the setting apparatus, for the case that a change resistance force is detected with the detection apparatus, is pre-set by a user so that the operating mode change is stipulated selectively into the operating mode of increased repeating frequency in which the repeating frequency of the repetitive thrust movement compared with the repeating frequency is increased before detection of the changed resistance force, or is stipulated in the operating mode of decreased repeating frequency in which the repeating frequency of the repetitive thrust movement compared with the repeating frequency is decreased before detection of the changed resistance force.

The invention concerns embodiments where, with the help of the setting apparatus, by the user, only the pre-setting of the change to the operating mode of increased repeating frequency/decreased repeating frequency is enabled, and this means that the setting apparatus for the case of increased resistance force allows only the selection between operating mode change or no operating mode change. However, embodiments are also covered by the invention where the user, for the case of increased resistance force, can select between two modes of the operating mode change with the help of the setting apparatus, namely a change into the operating mode of increased repeating frequency and a change into the operating mode of decreased repeating frequency, insofar as the user carries out a pre-setting. The operating modes of increased/decreased repeating frequency can each have a multiple-stage configuration so that several operating modes of increased repeating frequency and/or several operating modes of decreased repeating frequency are available, and this can be done with the help of a suitable selection switch.

During the extension and retraction phases of the puncturing means, the tip of the puncturing means during retraction is either drawn back through an opening into the housing or remains in front of the housing opening outside of the housing. In this way, particularly an operating mode is realizable where at least the tip of the puncturing means during operation remains constantly outside the housing of the handheld device, even if a forward/backward motion of the puncturing means is repeatedly carried out.

The elements of the driving device can be formed both in a handheld device for holding the needle as well as in a control device normally envisaged for controlling the handheld device. The handheld device and the control device are connected by way of a control cable, which normally comprises also a voltage supply line in order to make available an operating voltage formed in the control device at the drive means. The drive means are located in the handheld device and these drive means can comprise a motor in particular. Other elements of the driving device such as the control apparatus can be arranged in the handheld device or in the control device. The detection apparatus is formed in the handheld device or in the control device, particularly depending on which parameter is being detected. If a speed at the motor is to be measured, the detection apparatus can be arranged in the handheld device. If, however, for a possible embodiment the power input is to be evaluated as a parameter, the detection of this measuring value can be performed in the control device. The setting apparatus and the control apparatus can be, in each case, selectively integrated in the control device or the handheld device.

A substantial advantage which is obtained with the invention compared to the state of the art is the fact that the user of the driving device for the device for local puncturing of the skin is given the possibility of adapting to individual requirements when treating the skin where, for the case of changed skin characteristics, an automatic operating mode change can be set in advance so that the repeating frequency of the repetitive thrust movement is increased/decreased when performing local puncturing of the skin. The pre-setting can be carried out by the user in accordance with the various requirements and his wishes. Moreover, the introduction of a cosmetic or medical active substance over the skin with the help of the local puncturing can be envisaged also. The user friendliness of the devices is improved in this way. The person operating the device can fully concentrate on the puncturing of the skin because, in the event of a changed resistance force, i.e. a changed skin surface, the switchover to the operating mode increased/decreased repeating frequency takes place automatically without any necessity for an additional intervention by the operating persons. When using the device, a change of the operating mode can take place several times when changing several times between various types of skin sections.

If there is a transition to a harder skin, the invention helps to prevent the needle from sticking in position, and this is achieved by means of the automatic changeover to an operating mode with a changed frequency.

The resistance to the puncturing means will increase when the puncturing means enters the skin. This will allow the preparation of a pre-setting according to the requirements of the desired result. In the field of tattooing, as an example, there are two effects described as lining and shading. During lining, a consistent solid line is the desired result, whereas the desired result of shading is areas of more or less density to achieve a three dimensional effect. Thus the user desires a full or increased needle frequency for lining when entering the skin. In contrast, the needle frequency should drop when entering the skin for the purposes of shading.

Controlled by the control apparatus, the operating mode change is effected for various embodiments of the invention according to the pre-setting, either automatically or after the control apparatus has detected an acknowledgement of the operating mode change by the user, for example where a touch signal is awaited. In the latter case and with the help of the control apparatus, an optic or acoustic signal is preferably produced, which indicates the operating mode change to the user so that the user can acknowledge this.

With a purposeful embodiment of the invention, it is envisaged that the detection apparatus is configured for the purpose of detecting as a parameter a power input of the drive means. If the resistance force acting against the repetitive thrust movement is reduced or increased during the extension, this leads to a change of the power input to the drive means. For this reason, this parameter is a reliable indicator for the change of the resistance force.

The rotational speed of components or machine parts is an exactly detectable measurement variable with the help of conventional sensors. For this reason, and for a preferred embodiment of the invention, it is envisaged that the detection apparatus is configured for the purpose of detecting a rotational speed of the drive means as a parameter. Motors are frequently used as drive means where these motors produce a rotational movement, which is then converted, with the help of coupling or gear means, into a linear repetitive movement for the retraction/extension of the needle or the needle system in the device for local puncturing of the skin.

With the use of a rotating motor as a drive means, an advantageous further development of the invention envisages that the detection apparatus is configured in order to detect a commutation frequency as a parameter at the rotating motor. The commutation frequency as such is proportional to the speed of the rotating motor which changes with a change of the resistance force.

It can also be envisaged to detect the frequency of the strokes of the thrust movement as a parameter for the extension of the needle.

In order to keep the conditions during local puncturing at a continually reproducible status to the greatest possible extent, particularly for applying the permanent make-up or the tattoo, a further development of the invention envisages that the drive means are configured in order to maintain at a substantially constant level the repeating frequency before the detection of the changed resistance force, in the operating mode increased repeating frequency and in the operating mode decreased repeating frequency. A constant repeating frequency is obtained by means of a re-regulation of the electric parameter (s) of the drive means, for example the power input and/or the voltage applied at the drive motor.

There is the possibility of evaluating the detected parameter not only qualitatively, meaning with regard to a change, but also quantitatively with the help of the control means. In relation thereto, a purposeful embodiment of the invention envisages that the control apparatus is configured in order to stipulate, for the operating mode change, the increased/reduced repeating frequency in the operating mode increased repeating frequency/reduced repeating frequency as a factor of one or several measuring values for the detected parameter. Depending on a quantitative evaluation of the detected parameter, the repeating frequency can be stipulated for operating the device after the operating mode change. For example, certain threshold values can be stipulated for the parameter, for which then a related repeating frequency to be set is determined in each case. In this way, yet another further developed individualization of the operating mode is made possible subject to the application conditions, particularly those of the skin characteristics.

For one embodiment of the invention, it can be preferably envisaged that the control apparatus is configured in order to change the operating mode into the operating mode of increased repeating frequency/reduced repeating frequency, pre-set by means of the setting apparatus, if the detected parameter indicates an increase of the resistance force. In this way, it is enabled to automatically accomplish an operating mode change upon transition to "harder skin". In particular, it is important for such a transition to accomplish an adaptation to the changed characteristics of the skin surface because the conditions change for the puncturing of the skin. Moreover, the situation demands the particular attention and concentration of the operating persons for the puncturing of the skin, without having to observe the repeating frequency in addition.

In conjunction with the dependent claims of the method for operating a driving device for a device for the local puncturing of a skin, particularly for the application of permanent make-up or a tattoo, the statements pertaining to advantages apply accordingly in relation to the relevant claims with reference to the driving device.

DESCRIPTION OF PREFERRED EMBODIMENTS OF THE INVENTION

Figure 2:
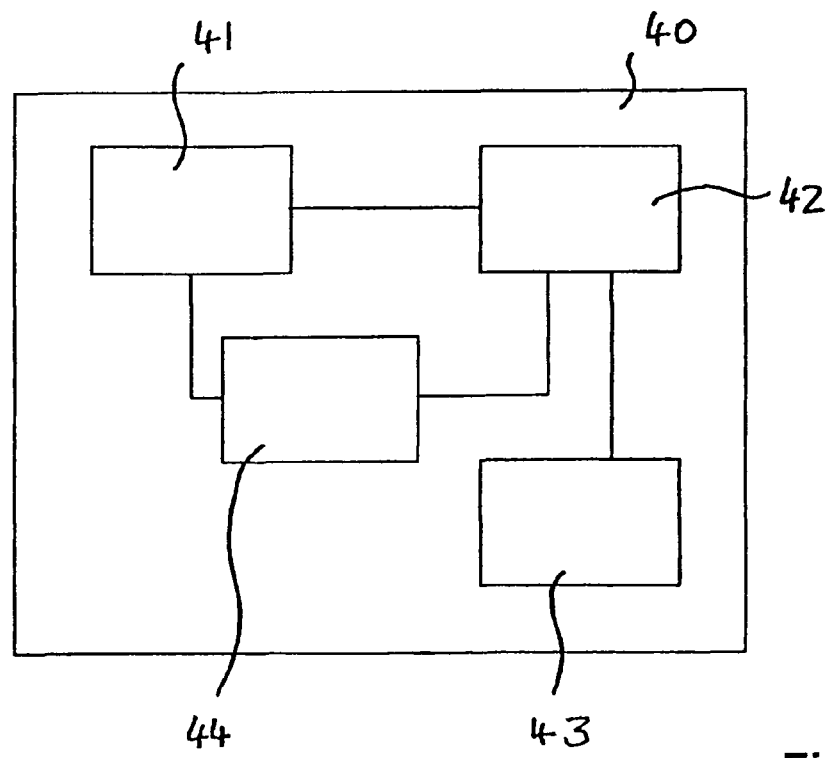

The invention will now be described by way of exemplary embodiments with reference to figures of the drawing in which:

FIG. 1 a schematic cross-sectional view of a device for the local puncturing of a skin, particularly for the application of permanent make-up or a tattoo, with a driving device and a module with puncturing means coupled to this; and FIG. 2 a schematic block view of elements of a drive apparatus.

FIG. 1 shows schematically a cross-sectional view of a device 1 for the local puncturing of a skin, particularly for the application of permanent make-up or a tattoo, or for the introduction of a medical or a cosmetic active substance, with a handheld device 10 and a control device 30 connected to the handheld device by way of a cable 20. A drive module 2 and a module 3 coupled to this are arranged at the handheld device 10. The module 3 can be detachable or solidly connected to the drive module 2. A detachable design has the advantage that the module 3 is usable with various drive modules and it can also be executed as a disposable module.

With the help of the drive module 2, a drive force is made available, for example by means of a rotating motor or a motor driven by way of magnetic coils. Such equipment for producing a drive force is known in various designs and is not explained here in greater detail for that reason.

The produced drive force is made available in conjunction with a rotational, tilting, linear movement or similar. The drive force is routed into a repeating thrust movement, as shown in FIG. 1 with the help of an arrow A. As a result of the repeating thrust movement, a needle 4 which can be either a single needle or a needle system with several needles is extended or retracted through an opening 5 in a housing 6.

The needle 4 is located in a needle shaft 7. When the needle 4 extends, the skin undergoing treatment is punctured so that, for example, the color material for establishing the permanent make-up or the tattoo can penetrate the skin surface. During the puncturing process of the skin, the needle 4 is confronted by a resistance force dependent on one of the characteristics of the skin surface.

The needle 4 can be coupled directly or by way of the needle shaft 7 to coupling/gear means (not shown) of the drive module 2, so that the retraction of the needle 4 after puncturing the skin takes place by means of the backward movement of the coupling/gear means. It can be alternatively envisaged that the needle is drawn back with the help of restoring means.

A driving device 40 with elements is envisaged with which the layout of the repetitive thrust movement can be set automatically in dependence of the operating conditions and which are shown in FIG. 2 with the help of schematic block view. The elements of the driving device 40 can be formed in the handheld device 10 and/or in the control device 30. With the help of a detection apparatus 40, measuring values for a parameter are detected, which characterizes the resistance force of the skin surface acting against the needle 4 (compare FIG. 1). These can be, for example, the rotational speed of a component or machine part of drive means 41 or the current/voltage input of the drive means 41. Both values change if the resistance force onto the needle 4 increases or decreases.

If such a change of the resistance force is determined, the control apparatus 42 which is coupled to the drive means 41 and to the detection apparatus 44 initiates an operating mode change of the drive means 41 so that the procedure continues with an operating mode of increased repeating frequency of the repetitive thrust movement or with an operating mode of reduced repeating frequency of the repetitive thrust movement. The repeating frequency is increased/decreased in comparison to a repeating frequency before detection of the change of the resistance force.

The switchover into one or the other changed operating modes is effected in dependence of a setting status of a setting apparatus 43, which is connected to the control apparatus 42. The setting apparatus 43 is, for example, executed as a momentary contact switch, slide switch or rotary switch, connected as required with a display unit, so that the operating personnel can stipulate with the help of the setting apparatus 43 into which operating mode the automatic change occurs when a change of the resistance force onto the repetitive thrust movement is determined. For example, it can be envisaged that a repeating frequency of 120 Hz is set in a normal or initial operating mode. If a change of the resistance force is detected, the procedure should be continued with a frequency of 130 Hz in the case of a change into the operating mode with increased repeating frequency, and with a repeating frequency of 110 Hz in the case of a change into the operating mode with decreased repeating frequency. Such an operating mode change should then take place in particular when an increase of the resistance force is determined, indicating the transition into a skin area that is harder.

With the help of the setting apparatus 43, at least two operating modes in each case with increased repeating frequency/decreased repeating frequency can also be made available for a user selection. Corresponding selection switches are available in a variety of designs. In a particularly plain style, the setting apparatus 43 gives the user the option of merely pre-setting a certain operating mode change or to do without it.

The driving device 40, particularly with the use of the components shown in FIG. 2, is preferably configured in such a way that the repeating frequency is kept essentially constant in the various operating modes. This is effected purposefully by way of a reregulation of the current and/or voltage input of the drive means 41.

The features of the invention as disclosed in this description, in the claims and in the drawings can be of significance both individually as well as in random combination for the realization of the invention in its various embodiment forms.

This application claims priority to European Patent Application No. 05 015074.7 and this application is hereby incorporated herein by reference.

What is claimed is:

1. A device for the local puncturing of a skin comprising:
a puncturing mechanism;
a drive mechanism producing a repetitive thrust movement which is for the retraction/extension of the puncturing mechanism;
a detection apparatus detecting a parameter indicative of a resistance force acting against the puncturing mechanism;
a setting apparatus having multiple present conditions corresponding to different operation modes that are operable when said detection apparatus measures a change in the resistive force, the different operation modes including 1) an increased frequency mode where a frequency of the repetitive thrust movement is increased when said detection apparatus measures an increased resistive force, and 2) a reduced frequency mode where a frequency of the repetitive thrust movement is reduced when said detection apparatus measures an increased resistive force; and
a control apparatus coupled to the detection apparatus and the setting apparatus,
wherein depending on the preset condition of the setting apparatus, said control apparatus automatically causes the increased frequency of the increased frequency mode or the reduced frequency of the reduced frequency mode when said detection apparatus measures an increased resistive force.

2. The driving device according to claim 1, wherein the detection apparatus is configured in order to detect as the parameter a power input of the drive mechanism.

3. The driving device according to claim 1, wherein the detection apparatus is configured in order to detect as the parameter a frequency of the drive mechanism.

4. The driving device according to claim 1, wherein the drive mechanism comprises a brush motor, and the detection apparatus is configured in order to detect a commutation frequency of the brush motor as the parameter.

5. The driving device according to claim 1, wherein the drive mechanism is configured in order to maintain at an essentially constant level the frequency before the detection of the changed resistance force, in the operating mode of increased frequency and in the operating mode reduced frequency.

6. The driving device according to claim 1, wherein the control apparatus is configured in order to stipulate the respective increased/reduced frequency of the increased/reduced frequency mode in dependence of at least one measuring value for the detected parameter.

7. The driving device according to claim 1, wherein the increased frequency mode corresponds to a mode for lining wherein a frequency of the device is increased when entering the skin and the decreased frequency mode corresponds to a mode for shading wherein a frequency of the device is reduced when entering the skin.

* * * * *